United States Patent [19]

Nakamori et al.

[11] Patent Number: 4,946,781

[45] Date of Patent: Aug. 7, 1990

[54] RECOMBINANT DNA, BACTERIA CARRYING SAID RECOMBINANT DNA AND A PROCESS FOR PRODUCING L-THREONINE OR L-ISOLEUCINE USING SAID BACTERIA

[75] Inventors: Shigeru Nakamori, Yokohama; Hiroshi Takagi, Kawasaki; Masaaki Ishida, Kawasaki; Takaaki Sato, Kawasaki; Kiyoshi Miwa, Matsudo; Konosuke Sano, Tokyo, all of Japan

[73] Assignee: Ajinomoto Co., Inc., Tokyo, Japan

[21] Appl. No.: 153,488

[22] Filed: Feb. 3, 1988

Related U.S. Application Data

[63] Continuation of Ser. No. 649,747, Sep. 12, 1984, abandoned.

[30] Foreign Application Priority Data

Sep. 14, 1983 [JP] Japan ................................. 58-170005

[51] Int. Cl.$^5$ ..................... C12P 13/08; C12P 13/06; C12N 1/20; C12N 15/00
[52] U.S. Cl. .................................. 435/115; 435/116; 435/252.32; 435/320; 435/840; 435/843; 935/60

[58] Field of Search ................. 435/115, 116, 172.3, 435/320, 252.32, 840, 843; 935/60

[56] References Cited

U.S. PATENT DOCUMENTS 4,601,983 7/1986 Nakamori et al. .................. 435/115

FOREIGN PATENT DOCUMENTS 0082485 6/1983 European Pat. Off. ......... 435/172.3

OTHER PUBLICATIONS

Lynn, S. et al., *J. Bacteriology*, vol. 152, pp. 363–371, 1982.

*Primary Examiner*—Jayme A. Huleatt
*Attorney, Agent, or Firm*—Oblon, Spivak, McClelland, Maier & Neustadt

[57] ABSTRACT

A recombinant DNA molecule comprising a plasmid vector having operationally inserted therein a gene coding for homoserine kinase is disclosed along with bacteria containing this recombinant DNA molecule and methods of using these bacteria to produce amino acids in large quantities.

6 Claims, 3 Drawing Sheets

RECOMBINANT DNA, BACTERIA CARRYING SAID RECOMBINANT DNA AND A PROCESS FOR PRODUCING L-THREONINE OR L-ISOLEUCINE USING SAID BACTERIA

This application is a Continuation of application Ser. No. 06/649, filed on Sep. 12, 1984, now abandoned.

BACKGROUND OF THE INVENTION

1. Field of the Invention:

The present invention relates to a recombinant DNA having inserted therein a gene coding for homoserine kinase, to bacteria carrying the recombinant DNA and to processes for producing L-threonine and L-isoleucine using the bacteria.

2. Description of the Prior Art:

Among the enzymes participating in the formation of L-threonine and L-isoleucine, the enzyme homoserine kinase (hereinafter referred to as "HK") is an enzyme which catalyzes the formation of phospho-homoserine from L-homoserine, an intermediate in the formation of L-threonine or L-isoleucine.

SUMMARY OF THE INvENTION

It is an object of this invention to provide a recombinant DNA molecule useful for increasing the rate of production of L-threonine or L-isoleucine.

It is a further object of this invention to provide bacteria carrying the recombinant DNA molecule and to provide methods for producing L-threonine and L-isoleucine using these bacteria.

These and other objects of the invention as will hereinafter become more readily apparent have been accomplished by providing a recombinant DNA molecule comprising a plasmid vector and a gene coding for homoserine kinase operationally inserted therein, wherein said plasmid vector is capable of propagating and said gene is capable of being expressed in a Coryneform bacterium. Also disclosed as part of the present invention are bacterial transformants containing said recombinant DNA and a process for producing amino acids using said bacteria.

BRIEF DESCRIPTION OF THE DRAWINGS

A more complete appreciation of the invention and many of the attendant advantages thereof will be readily obtained by reference to the following detailed description when considered in connection with the accompanying drawings, wherein.

DESCRIPTION OF THE PREFERRED EMBODIMENTS

Figure 1:
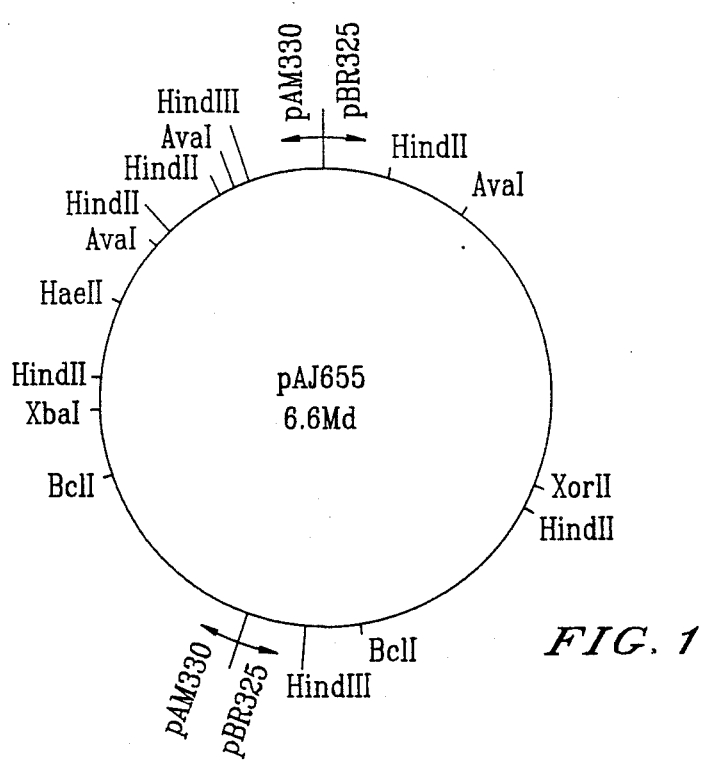
FIG. 1 is a restriction map of composite plasmid pAJ 655.

The present inventors have paid special attention to Cornyeform bacteria known for producing a great amount of L-threonine and started their present research to further increase productivity by taking advantage of recombinant DNA techniques. The inventors have succeeded in isolating, from Coryneform bacteria, a gene coding for HK which participates in production of L-threonine and L-isoleucine (hereinafter referred to as "HK gene"). In addition, when the gene is connected with a plasmid vector capable of propagating in cells of Coryneform bacteria and is introduced into the cells of a Coryneform bacterium, a remarkably increased production of L-threonine and L-isoleucine occurs.

Coryneform bacteria are aerobic, Gram positive rods, are non-acid fast, and are described in Bergey's *Manual of Determinative Bacteriology,* 8th Edition, 599 (1974). Among them there are known wild strains producing L-glutamic acid in a large amount, particularly as shown below. These strains are closely related members of the genera Brevibacterium (family Brevibacteriaceae) and Corynebacterium and Microbacterium (both family Corynebacteriaceae) and will be referred to herein as "Coryneform bacteria."

Brevibacterium divaricatum ATCC 14020
Brevibacterium saccarolyticum ATCC 14066
Brevibacterium immariophilum ATCC 14068
Brevibacterium lactofermentum ATCC 13869
Brevibacterium roseum ATCC 13825
Brevibacterium flavum ATCC 13826
Brevibacterium thiogenitalis ATCC 19240,
Corynebacterium acetoacidophilum ATCC 13870
Corynebacterium acetoglutamicum ATCC 15806
Corynebacterium callunae ATCC 15991
Corynebacterium glutamicum ATCC 13032 and 13060
Corynebacterium lilium ATCC 15990
Corynebacterium melassecola ATCC 17965
Microbacterium ammoniaphilum ATCC 15354

Coryneform bacteria also include, in addition to the aforesaid wild strains having glutamic acid productivity, mutants including those which have lost glutamic acid productivity.

Isolation of the HK gene can be conducted by any known method of gene isolation, of which the following method is a preferred method. Firstly, a chromosomal gene is extracted from a strain of Coryneform bacteria carrying an HK gene (there can be utilized, for example, the method of H. Saito and K. Miura, *Biochem. Biophys. Acta,* 72, 619 (1963)). The gene is then cleaved with an appropriate restriction enzyme and inserted into a plasmid vector capable of propagating in Coryneform bacteria. An HK-deficient mutant of Coryneform bacteria is transformed with the resulting recombinant DNA. Bacterial strains which come to possess HK-forming activity are isolated, and an HK gene can be isolated therefrom in quantity.

To cleave the chromosomal genes, a wide variety of restriction enzymes can be employed. The degree of cleavage can be controlled by controlling the time for the cleavage reaction, the temperature, etc., as is well known to those skilled in the art.

Figure 2:
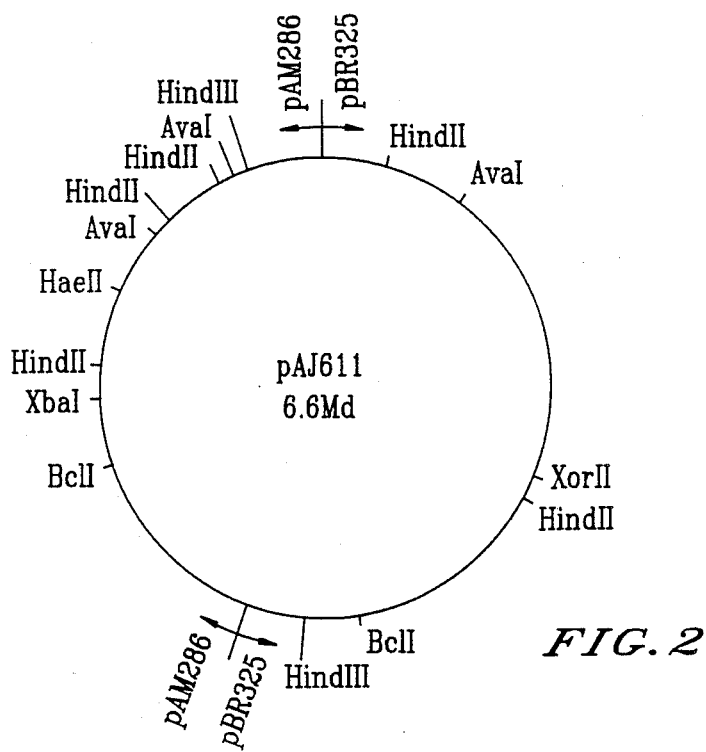
FIG. 2 is a restriction map of composite plasmid pAJ 611.
Figure 3:
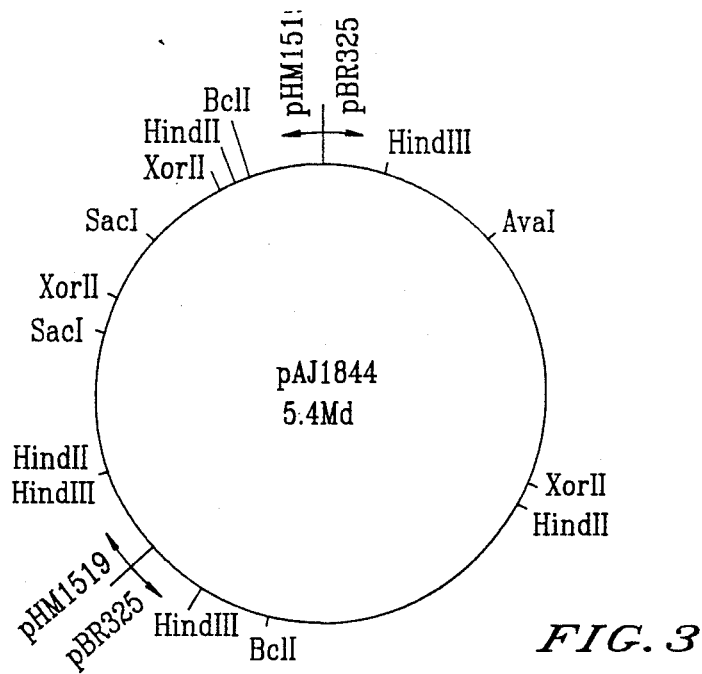
FIG. 3 is a restriction map of composite plasmid pAJ 1844.
Figure 4:
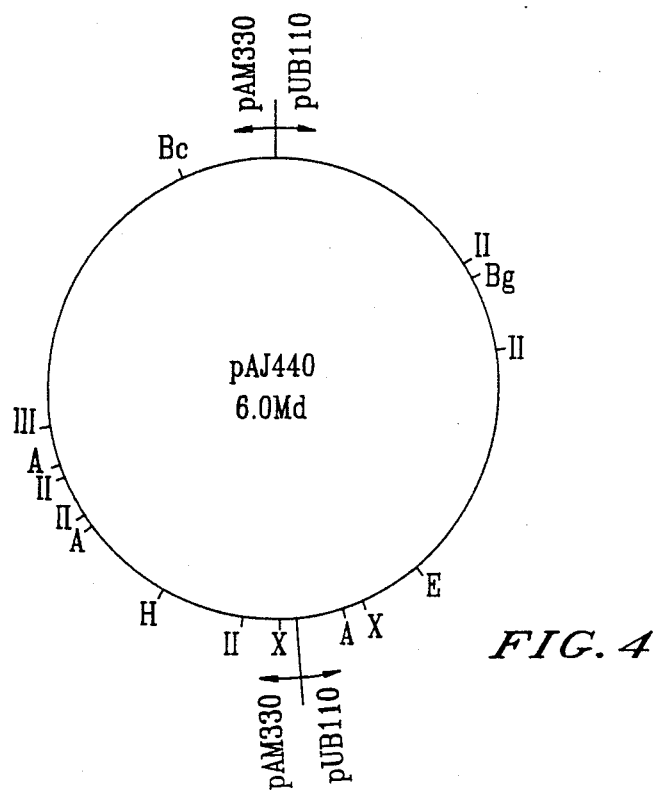
FIG. 4 is a restriction map of composite plasmid pAJ 440.
Figure 5:
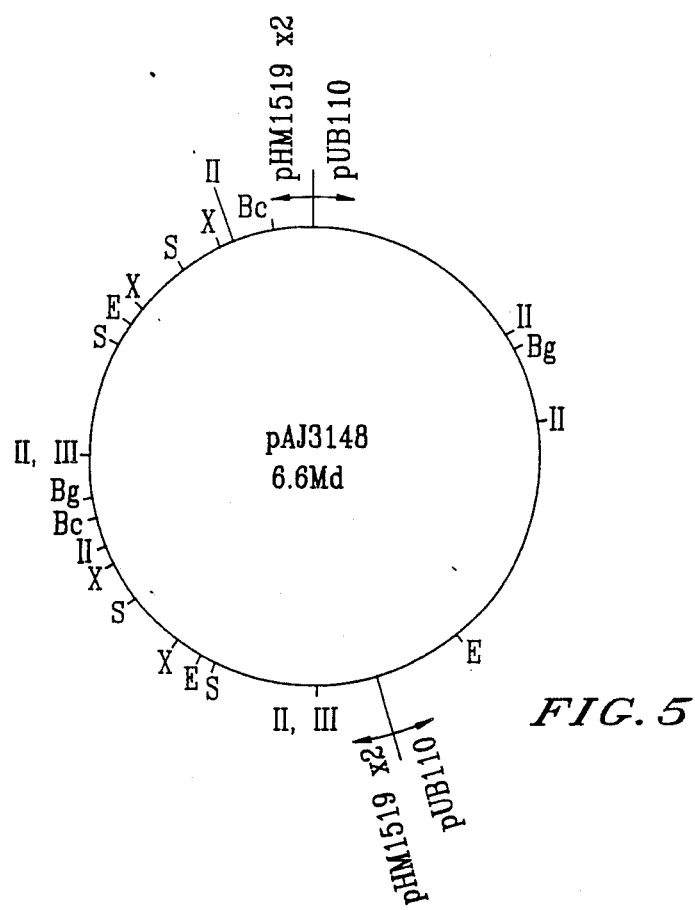
FIG. 5 is a restriction map of composite plasmid pAJ 3148.

The plasmid vector used in the present invention can be any vector as long as it can be propagated in cells of Coryneform bacteria. Specific examples include the following:

(1) pAM 330: see Japanese Published Unexamined patent application No. 58-67699
(2) pHM 1519: see Japanese Published Unexamined patent application No. 58-77895
(3) pAJ 655:
   (a) host bacteria: *Escherichia coli* AJ 11882 (FERM-P 6517=FERM-BP 136, etc.)
   (b) molecular weight: 6.6 megadaltons (c) restriction map of restriction enzyme: see FIG. 1
(d) properties: composite plasmid of pAM 330 and pBR 325 (Gene, 4, 121 (1978)) giving chloramphenicol resistance to the host (4) pAJ 611:
 (a) host bacteria: *Escherichia coli* AJ 11884 (FERM-P 6519=FERM-BP 138, etc.)
 (b) molecular weight: 6.6 megadaltons
 (c) restriction map of restriction enzyme: see FIG. 2
 (d) properties: composite plasmid of pAM 218 and pBR 325 giving chloramphenicol resistance to the host (5) pAJ 440:
 (a) host bacteria: *Bacillus subtilis* AJ 11901 (FERM-BP 140=ATCC 39139, etc.)
 (b) molecular weight: 6.0 megadaltons
 (c) restriction map of restriction enzyme: see FIG. 4
 (d) properties: composite plasmid of pAM 330 and pUB 110 (*J. Bacteriol.*, 134, 318 (1978)) giving kanamycin resistance to the heat (6) pAJ 1844:
 (a) host bacteria: *Escherichia coli* AJ 11883 (FERM-P 6519=FERM-BP 137, etc.)
 (b) molecular weight: 5.4 megadaltons
 (c) restriction map of restriction enzyme: see FIG. 3
 (d) properties: composite plasmid of pHM 1519 and pBR 325 giving chloramphenicol resistance to the host (7) pAJ 3148:
 (a) host bacteria: *Corynebacterium glutamicum* SR 8203, ATCC 39137, etc.
 (b) molecular weight: 6.6 megadaltons
 (c) restriction map of restriction enzyme: see FIG. 5
 (d) properties: composite plasmid of pHM 1519 and pUB 110 giving kanamycin resistance to the host Other examples of plasmids capable of propagating in cells of Coryneform bacteria include pCG 1 (Japanese Published Unexamined patent application No. 57-134500), pCG 2 (Japanese Published Unexamined patent application No. 58-35197), and pCG 4 and pCG 11 (Japanese Published Unexamined patent application No. 57-183799). All of these plasmids can be used in the practice of the present invention.

The vector DNA is cleaved by the same restriction enzyme used for cleavage of the chromosomal gene, or the vector DNA is connected with on oligonucleotide having a complementary base sequence at its respective terminals for the chromosomal DNA cleavage fragment and the cleaved vector DNA. The resulting composite is then subjected to a ligation reaction to join the plasmid vector and the chromosomal DNA fragment. When a gene is inserted by this or any other method in the sense direction and in proper reading frame so that the HK enzyme is expressed when the plasmid is transcribed and translated by the genetic machinery of a cell in which the plasmid is inserted, the gene is said to be "operationally inserted" into the plasmid vector.

The incorporation of the thus-obtained recombinant DNA (comprising the chromosomal DNA and the vector plasmid) into recipients belonging to Coryneform bacteria can be done by any known method, of which the following are preferred examples. The recipient cells can be treated with calcium chloride to increase the permeability of DNA, as is reported regarding *Escherichia coli* K-12 (Mandel, M. and Higa, A., *J. Mol. Biol.* 53, 159 (1970)). Alternately, the recombinant DNA can be incorporated at a stage of growth (the so-called competent cell) when cells become capable of incorporating DNA, as is reported for *Bacillus subtilis* (Duncan, C. H., Wilson, G. A. and Young, F. E., Gene, 1, 153 (1977)). The plasmids can also be incorporated into the DNA recipients by forming protoplasts or spheroplasts of the DNA recipients which easily incorporate plasmid DNA, as is known for *Bacillus subtilis*, Actinomycetes and yeast (Chang, S. and Cohen, S. N., *Molec. Gen. Genet.*, 168, 111 (1979); Bibb, M. J., Ward, J. M. and Hopwood, O. A., *Nature*, 274, 398 (1978); Hinnen, A., Hicks, J. B. and Fink, G. R., *Proc. Natl. Acad. Sci. USA*, 75, 1929 (1978)).

In the protoplast method, a sufficiently high frequency can be obtained even by the method used for *Bacillus subtilis* described above. Further, there can be properly used a method described in Japanese Published Unexamined patent application No. 57-183799 which comprises incorporating DNA into protoplast of the genus Corynebacterium or the genus Brevibacterium in the presence of polyethylene glycol or polyvinyl alcohol and divalent metal ions. Equivalent effects can also be obtained by a method of promoting the incorporation of DNA by the addition of carboxymethyl cellulose, dextran, Ficoll, Pluronic F68 (Celva Company), etc., instead of polyethylene glycol or polyvinyl alcohol.

After transformation, bacterial strains that acquire HK productivity or express properties as markers further possessed by the plasmid vectors are isolated as the desired transformants. Such transformants carry the recombinant DNAs harbouring the HK gene. To isolate the recombinant DNA, for example, bacteria are lysed by treating with lysozyme and SDS (sodium dodecyl sulfate) and then treated with phenol. Then a 2-fold volume of ethanol is added to thereby precipitate and recover DNAs.

The methods of culturing the L-threonine- or L-isoleucine-producing bacteria thus obtained are conventional and are similar to the methods for the cultivation of conventional L-threonine- or L-isoleucine-producing bacteria. That is, the culture medium can be a conventional medium containing carbon sources, nitrogen sources, and inorganic ions and, when required, organic micro-nutrients such as vitamins and amino acids. Examples of carbon sources include glucose, sucrose, lactose and starch as well as hydrolysates which contain these carbon sources such as whey and molasses. Examples of nitrogen sources include gaseous ammonia, aqueous ammonia, ammonium salts and others.

Cultivation is conducted under aerobic conditions in which the pH and the temperature of the medium are adjusted to a suitable level, and cultivation is continued until the formation and accumulation of L-threonine or L-isoleucine cease.

Thus, markedly high amounts of L-threonine or L-isoleucine are formed and accumulated in the culture medium. To recover L-threonine or L-isoleucine from the culture medium, any conventional manner is applicable, such as crystallization or absorption during column chromatography.

In addition to the above general procedures which can be used for preparing amino-acid-producing bacteria in accordance with the practices of this invention, other known techniques and modifications thereof can be used in carrying out the practice of the invention. In particular, techniques relating to genetic engineering have recently undergone exclusive growth and development. Many recent U.S. patents disclose plasmids, genetically engineered microorganisms, and methods of conducting genetic engineering which can be used in the practice of the present invention. For example, U.S. Pat. No. 4,273,875 discloses a plasmid and a process of isolating the same. U.S. Pat. No. 4,304,863 discloses a process for producing bacteria by genetic engineering in which a hybrid plasmid is constructed and used to transform a bacterial host. U.S. Pat. No. 4,419,450 discloses a plasmid useful as a cloning vehicle in recombinant DNA work. U.S. Pat. No. 4,362,867 discloses recombinant cDNA construction methods and hybrid nucleotides produced thereby which are useful in cloning processes. U.S. Pat. No. 4,403,036 discloses genetic reagents for generating plasmids containing multiple copies of DNA segments. U.S. Pat. No. 4,363,877 discloses recombinant DNA transfer vectors. U.S. Pat. No. 4,356,270 discloses a recombinant DNA cloning vehicle and is a particularly useful disclosure for those with limited experience in the area of genetic engineering since it defines many of the terms used in genetic engineering and the basic processes used therein. U.S. Pat. No. 4,336,336 discloses a fused gene and a method of making the same. U.S. Pat. No. 4,349,629 discloses plasmid vectors and the production and use thereof. U.S. Pat. No. 4,332,901 discloses a cloning vector useful in recombinant DNA. Although some of these patents are directed to the production of a particular gene product that is not within the scope of the present invention, the procedures described therein can easily be modified by utilizing an HK gene in place of the gene described specifically in the patents.

All of these patents as well as all other patents and other publications cited in this disclosure are indicative of the level of skill of those skilled in the art to which this invention pertains and are all herein incorporated by reference.

The invention now being generally described, the same will be better understood by reference to certain specific examples which are included herein for purposes of illustration only and are not intended to be limiting of the invention or any embodiment thereof, unless specified.

Example (1) Preparation of chromosomal DNA carrying an HK gene:

The mutant AJ 11188 (FERM-P 4190) resistant to $\alpha$amino-$\beta$-hydroxyvaleric acid (as described in Japanese Published Examined patent application No. 56-3038) *Brevibacterium lactofermentum* ATCC 13869 was inoculated on 1 liter of CMG medium ("complete medium, glucose": peptone 1 g/dl, yeast extract 1 g/dl, glucose 0.5 g/dl and NaCl 0.5 g/dl; adjusted pH to 7.2) and subjected to shake culture at 30° C. for about 3 hours to harvest cells at an exponential growth phase. After the cells were lysed by lysozyme and SDS, chromosomal DNAs were extracted and purified by a conventional phenol treatment to finally obtain 3.5 mg of DNAs.

(2) Preparation of vector DNA:

Using pAJ 1844 (molecular weight, 5.4 megadaltons) as a vector, its DNAs were prepared as follows:

Firstly, *Brevibacterium lactofermentum* AJ 12037 (FERM-P 7234), having pAJ 1844 as a plasmid, was inoculated on 100 ml of the CMG medium and cultured at 30° C. to reach a late exponential growth phase. After the cells were lysed by lysozyme and SDS, they were ultracentrifuged at 30,000×g for 30 minutes to obtain the supernatant.

After treatment with phenol, a two-fold volume of ethanol was added to precipitate and harvest DNAs. The precipitates were dissolved in a small amount of a TEN buffer solution (20 mM tris hydrochloride, 1 mM EDTA, 20 mM NaCl; adjusted to pH 8.0). Then, they were subjected to agarose gel electrophoresis to fractionate and harvest approximately 15 μg plasmid DNA of pAJ 1844.

(3) Insertion of chromosomal DNA fragment into vector:

Chromosomal DNAs, 20 μg, obtained in part (1) above, and 10 μg of plasmid DNAs were individually treated at 37° C. for 1 hour with restriction endonuclease Pst I to fully cleave them. After heat treatment at 65° C. for 10 minutes, both reaction liquids were mixed, and the mixture was subjected to a ligation reaction between the DNA chains with DNA ligase derived from $T_4$ phage at 10° C. for 24 hours in the presence of ATP and dithiothreitol. After heat treatment at 65° C. for 5 minutes, a 2-fold volume of ethanol was added to the reaction liquid to precipitate and harvest DNAs after completion of the ligation reaction.

(4) Cloning of HK gene:

*Brevibacterium lactofermentum* (AJ 12078), which is deficient in the HK gene, was used as a recipient.

As a method for transformation, the protoplast transformation method was used. Firstly, the strain was cultured in 5 ml of CMG liquid medium to reach an early exponential growth phase. After adding 0.6 unit/ml of penicillin G thereto, shake culture was performed for a further 1.5 hour. The cells were harvested by centrifugation and washed with 0.5 ml of SMMP medium (pH 6.5) composed of 0.5 M sucrose, 20 mM maleic acid, 20 mM magnesium chloride and 3.5% Penassay broth (Difco). Then the cells were suspended in SMMP medium containing 10 mg/ml of lysozyme to cause protoplastation at 30° C. for 20 hours. After centrifugation at 6000×g for 10 minutes, the protoplasts were washed with SMMP and resuspended in 0.5 ml of SMMP. The thus-obtained protoplasts were mixed with 10 μg of DNAs prepared in part (3) above in the presence of 5 mM EDTA. After polyethylene glycol was added to the mixture to give a final concentration of 30%, the mixture was allowed to stand for 2 minutes at room temperature to incorporate DNAs into the protoplast. After the protoplasts were washed with 1 ml of SMMP medium, the protoplasts were resuspended in 1 ml of SMMP medium. The suspension was incubated at 30° C. for 2 hours to effect phenotypic expression. The culture liquid was spread on protoplast regeneration medium at pH 7.0. The protoplast regeneration medium contained, per one liter of distilled water, 12 g of tris(-hydroxymethyl)aminomethane, 0.5 g of KCl, 10 g of glucose, 8.1 g of $MgCl_2.6H_2O$, 2.2 g of $CaCl_2.2H_2O$, 4 g of peptone, 4 g of powdered yeast extract, 1 g of Casamino acid (Difco Company), 0.2 g of $K_2HPO_4$, 135 g of sodium succinate, 8 g of agar and 3 μg/ml of chloramphenicol.

After culturing at 30° C. for 2 weeks, approximately 10,000 colonies resistant to chloramphenicol appeared, which were replicated in a threonine-free medium (Thr-deficient medium: 2% glucose, 1% ammonium sulfate, 0,25% urea, 0,1% dihydrogen potassium phosphate, 0.04% magnesium sulfate heptahydrate, 2 ppm iron ions, 2 ppm manganese ions, 200 μg/l thiamine hydrochloride and 50 μg/l biotin; pH 7.0, agar 1.8%) to obtain 8 strains resistant to chloramphenicol and having the lost auxotrophy for threonine.

(5) Plasmid analysis of the transformant:

These strains were treated in a manner described in part (2) above to prepare the lysate. Plasmid DNAs were detected by agarose gel electrophoresis. Plasmids obviously larger than vector pAJ 1844 were detected from two strains. The typical strain was named AJ 12079 (FERM-P 7237)

(6) Retransformation:

In order to confirm that the HK gene was present on the recombinant plasmid (pAJ 211) in AJ 12079, Brevibacterium lactofermentum AJ 12078 was retransformed using this plasmid DNA.

Ten strains were selected from each of the thus-formed chloramphenicol-resistant colonies. Examination of auxotrophy for threonine indicated that the auxotrophy was lost in all of the colonies, and it became clear that the HK genes were present on the recombinant plasmids described above.

(7) Productivity of threonine and isoleucine with the transformant:

Plasmid pAJ 211 was introduced into Brevibacterium lactofermentum AJ 11188, a threonine-producing mutant resistant to α-amino-β-hydroxyvaleric acid, using the protoplast transformation method described above. A transformant was selected by chloramphenicol resistance. The strains thus obtained, AJ 12080 (FERMP 7238) and AJ 12079 mentioned above, were inoculated on 20 ml of threonine-producing medium consisting of 10 g/dl of glucose, 4.5 g/dl of $(NH_4)_2SO_4$, 0.1 g/dl of $KH_2PO_4$ 0.1 g/dl of $MgSO_4.7H_2O$, 2 ppm of $Fe^{2+}$, 2 ppm of $Mn^{2+}$, 300 μg/dl of thiamine . HCl, 10 μg/l of biotin, 45 mg/dl of soybean protein hydrolysate "Mieki" (as total nitrogen), pH 7.2, 5 g/dl of $CaCO_3$ separately sterilized, this medium being supplemented with L-homoserine for AJ 12078 and 12079, and with 25 mg/dl of L-isoleucine and 30 mg/dl of L-leucine for AJ 11188 and AJ 12080. These strains were shake cultured at 30° C. for 72 hours. After incubation, L-threonine in the supernatant centrifuged was quantitatively determined by microbioassay. The results are given in Table 1.

TABLE 1

| Strain | Amount of L-threonine accumulated | Amount of L-isoleucine accumulated |
|---|---|---|
| AJ 11188 | 1.24 g/dl | — |
| AJ 12080 (FERM-BP 579) | 1.86 g/dl | — |
| AJ 12078 | 0.0 mg/dl | 0.0 mg/dl |
| AJ 12079 (FERM-BP 578) | 10 mg/dl | 110 mg/dl |

Brevibacterium lactofermentum AJ 12078 was obtained by contacting Brevibacterium lactofermentum ATCC 13869 with 2,000 μg/ml of N-methyl-N'-nitro-N-nitrosoguanidine at 0° C. for 20 minutes for mutation treatment as a strain which could not grow on L-threonine deficient medium but could grow on Thr-deficient medium supplemented with 10 mg/dl of L-threonine. This strain did not show any accumulation of phosphohomoserine in its quantitative determination. AJ 12078 and AJ 11188 were easily obtained from AJ 12079 or AJ 12080, respectively, by removing the composite plasmid without injury to the host cells. That is, the plasmid is spontaneously expelled from host in some occasions or may also be removed by a "removing" operation (Bact. Rev., 36, p 361-405 (1972)). An example of the removing operation is as follows: A small number of cells (approximately $10^4$ cells per 1 ml) are inoculated on a medium containing acridine orange having a concentration (2 to 50 μg/ml) insufficient to inhibit growth of the host. Then, the cells are cultured at 27° to 35° C. overnight (J. Bacteriol., 88, 261 (1964)). The culture liquid is spread on agar medium followed by culturing at 27° to 42° C. overnight.

In the colonies appearing on the medium, strains from which plasmids had been removed were those showing sensitivity to chloramphenicol (10 μg/ml), namely AJ 12078 and AJ 11188.

The invention now being fully described, it will be apparent to one of ordinary skill in the art that many changes and modifications can be made thereto without parting from the spirit or scope of the invention as set forth herein.

What is new and desired to be secured by Letters Patent of the United States is:

1. A recombinant DNA molecule, comprising a vector and a gene coding for homoserine kinase operationally inserted therein, wherein said recombinant DNA molecule is capable of propagating and said gene is capable of being expressed in a coryneform bacterium, and wherein said gene is a chromosomal gene of Corynebacterium or Brevibacterium.

2. The recombinant DNA molecule of claim 1, wherein said vector is selected from the group consisting of pAM 330, pHM 1519, pAJ 655, pAJ 611, pAJ 440, pAJ 1844, pAJ 3148, pCG 1, pCG 2, pCG 4, and pCG 11.

3. A coryneform bacterium carrying a recombinant DNA molecule comprising a vector having operationally inserted therein a gene coding for homoserine kinase, wherein said gene is a chromosomal gene of Corynebacterium or Brevibacterium.

4. The cornyform bacterium of claim 3, wherein said vector is selected from the group consisting of pAM 330, pHM 1519, pAJ 655, pAJ 611, pAJ 440, pAJ 1844, pAJ 3148, pCG 1, pCG 2, pCG 4, and pCG 11.

5. A process for producing an amino acid by fermentation, which comprises:

(a) cultivating in a culture medium a coryneform bacterium carrying a recombinant DNA molecule comprising a vector having operationally inserted therein a gene coding for homoserine kinase, wherein said bacterium produces an amino acid selected from the group consisting of L-threonine and L-isoleucine, and wherein said gene is a chromosomal gene of Corynebacterium and Brevibacterium, and (b) isolating said amino acid from said culture medium.

6. The process of claim 5, wherein said vector is selected from the group consisting pAM 330, pHM 1519, pAJ 655, pAJ 611, pAJ 440, pAJ 1844, pAJ 3148, pCG 1, pCG 2, pCG 4, and pCG 11.

* * * * *